United States Patent
Weiner et al.

(10) Patent No.: US 7,598,041 B2
(45) Date of Patent: Oct. 6, 2009

(54) HIV-1 VPR INTERACTIONS WITH MITOCHONDRIAL APOPTOSIS INDUCING FACTOR AND METHODS OF USING THE SAME

(75) Inventors: David B. Weiner, Merion Station, PA (US); Karuppiah Muthumani, Cherry Hill, NJ (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/478,742

(22) PCT Filed: May 28, 2002

(86) PCT No.: PCT/US02/16731

§ 371 (c)(1),
(2), (4) Date: Aug. 2, 2004

(87) PCT Pub. No.: WO03/040415

PCT Pub. Date: May 15, 2003

(65) Prior Publication Data

US 2005/0026138 A1 Feb. 3, 2005

Related U.S. Application Data

(60) Provisional application No. 60/293,570, filed on May 25, 2001.

(51) Int. Cl.
G01N 33/53 (2006.01)
G01N 33/567 (2006.01)
A61K 38/00 (2006.01)
C12P 21/08 (2006.01)
A61K 49/00 (2006.01)

(52) U.S. Cl. .......................... 435/7.1; 435/7.8; 530/300; 530/388.4; 424/9.1

(58) Field of Classification Search ............... 435/5, 435/7.1, 7.2, 7.24, 974, 975; 530/329, 350
See application file for complete search history.

(56) References Cited

U.S. PATENT DOCUMENTS 5,780,220 A 7/1998 Weiner et al.
5,976,786 A 11/1999 Finkel et al.
6,060,587 A * 5/2000 Weiner et al. ................. 514/44

FOREIGN PATENT DOCUMENTS

WO WO94/19456 9/1994
WO WO98/35234 8/1998

OTHER PUBLICATIONS

Zhao et al. "Yeast Perspectives on HIV-1 VPR" Frontiers in Bioscience vol. 5, (Dec. 1, 2000) pp. 905-916.*
Jacotot E. et al. "The HIV-1 viral protein R induces apoptosis via a direct effect on the mitochondrial permeability transition pore". J Exp Med. Jan. 3, 2000;191(1):33-45.*
Daugas E. et al. "Apoptosis-inducing fctor (AIF): a ubiquitous mitochondrial oxidoreductase involved in apoptosis". FEBS Lett. Jul. 7, 2000;476(3):118-23. Review.*
Susin SA et al. "Molecular characterization of mitochondrial apoptosis-inducing factor". Nature. Feb. 4, 1999;397(6718):441-6.*
Kino T et al. "Partner molecules of accessory protein Vpr of the human immunodeficiency virus type 1", DNA and Cell Biology, 23(4):193-205, 2004.*
Genini, et al., "HIV Induces lymphocyte apoptosis by a p53-initiated, mitochondrial-mediated mechanism," FASEB J. (2001) 15:5-6.
Ferri, et al., "Mitochondrial control of cell death induced by HIV-1 encoded proteins," Ann. NY Acad. Sci. (2000) 926:149-164.
Ferri, et al., "Apoptosis control in syncytia induced by the HIV type-1 envelope glycoprotein complex: role of mitochondria and caspases," J. Exp. Med. (2000) 192:1081-1092.
T. Roumier et al., "The C-Terminal Moiety of HIV-1 Vpr Induces Cell Death via a Caspase-Independent Mitochondrial Pathway", Cell Death and Differentiation, 2002; 9(11):1212-1219.

* cited by examiner

*Primary Examiner*—Bo Peng
(74) *Attorney, Agent, or Firm*—Pepper Hamilton LLP

(57) ABSTRACT

Assays to identify Vpr/AIF interaction and translocation inhibitors are disclosed.

5 Claims, No Drawings

HIV-1 VPR INTERACTIONS WITH MITOCHONDRIAL APOPTOSIS INDUCING FACTOR AND METHODS OF USING THE SAME

CROSS REFERENCE TO RELATED APPLICATION

This application is a U.S. National Phase Application of PCT International Application PCT/US02/16731, filed May 28, 2002, which claims priority to provisional application Ser. No. 60/293,570, filed May 25, 2001.

FIELD OF THE INVENTION

The invention relates to the discovery that of HIV Vpr binds to AIF from mitochondria and to assays to identify modulators of the interaction.

BACKGROUND OF THE INVENTION

The HIV accessory protein Vpr has been identified as being capable of cell cycle arrest and the induction of apoptosis. This observation is described in PCT application PCT/US01/10028, which is incorporated herein by reference.

The interaction of HIV Vpr with the human cellular protein hVIP has been disclosed in PCT application PCT/US98/21432, which is incorporated herein by reference.

Mitochondrial apoptosis inducing factor has been identified.

There is a need for drug discovery screens and novel drugs to prevent or induce apoptosis and that are useful in the treatment of inflammatory disease and cancer.

SUMMARY OF THE INVENTION

The present invention relates to methods of identifying compounds that inhibit Vpr binding to AIF.

The present invention relates to methods of identifying compounds that inhibit the nuclear translocation of Vpr in the presence of AIF.

DETAILED DESCRIPTION OF PREFERRED EMBODIMENTS

It has been discovered that Vpr binds to AIF. It has been discovered that the complex formed by Vpr bound to AIF, which is normally found in the mitochondria, translocates to the nucleus of cells.

AIF is known to induces apoptosis by a non-caspase 9 pathway. Vpr is known to induce apoptosis by a caspase-9 pathway.

The discovery that Vpr binds to AIF provides the means to design and discover specific inhibitors. According to the present invention, Vpr and AIF are used to used to screen compounds for specific inhibitors. Inhibitors are useful as anti-HIV agents as well as agents for the treatment of inflammatory diseases and cancer. Purified Vpr and AIF may be used in drug screens to identify compounds which dissociate the complexes and inhibit the formation of complexes. Compounds may also be screened to identify those which inhibit the complex from translocating to the nucleus.

One having ordinary skill in the art can isolate the nucleic acid molecules that encode Vpr and AIF and insert them into expression vectors using standard techniques and readily available starting materials. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. The recombinant expression vectors of the invention are useful for transforming hosts which express the proteins Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of PAPA1 in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce proteins by routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

The expression vector including the DNA that encodes either Vpr or AIF is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate the Vpr or AIF that is produced using such expression systems. The methods of purifying protein from natural sources using antibodies which specifically bind to the proteins may be equally applied to purifying proteins produced by recombinant DNA methodology.

In addition to producing proteins by recombinant techniques, automated peptide synthesizers may also be employed to produce Vpr and/or AIF. Such techniques are well known to those having ordinary skill in the art and are useful if derivatives which have substitutions not provided for in DNA-encoded protein production.

Hybridomas which produce antibodies that bind to AIF or Vpr, and the antibodies themselves, are useful in the isolation and purification of AIF or Vpr and protein complexes that include AIF and Vpr. In addition, antibodies are specific inhibitors of AIF or Vpr. Antibodies which specifically bind to the respective protein may be used to purify that protein from natural sources using well known techniques and readily available starting materials. Such antibodies may also be used to purify the protein from material present when producing the protein by recombinant DNA methodology.

As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. In some embodiments, the antibodies specifically bind to an epitope of AIF or Vpr. Antibodies that bind to an epitope is useful to isolate and purify that protein from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly, for example, AIF, or an immunogenic fragment thereof, is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the protein, the hybridoma which produces them is cultured to produce a continuous supply of antibodies. Antibodies against AIF are commercially available from Chemicon International (Temecula, Calif.) catalog #AB16501.

The present invention relates to methods of identifying anti-HIV compounds and compounds useful to treat cancer and autoimmune diseases. According to this aspect, the Vpr or a fragment of Vpr known to interact with AIF is contacted with AIF or a fragment of AIF which interacts with Vpr in the presence of a test compound. The affininty of the Vpr or a fragment thereof to the AIF or fragment thereof is measured and compared to the affinity of the Vpr or a fragment thereof to the AIF or fragment thereof in the absence of a test compound. Compounds which can disrupt the binding of AIF to Vpr may be useful as anti-HIV compounds or compounds useful to treat cancer and autoimmune diseases. An example of a positive control in this drug screen assay would be anti-Vpr antibodies which competitively bind to Vpr with respect to AIF. Another example of a positive control in this drug screen assay would be anti-AIF antibodies which competitively bind to AIF with respect to Vpr. Such antibodies are useful as known compounds that disrupt the Vpr/AIF interaction. Known quantities of Vpr and AIF may be combined under conditions suitable for binding. In some embodiments of the invention, the preferred concentration of test compound is between 1 µM and 500 µM. A preferred concentration is 10 µM to 100 µM. In some preferred embodiments, it is desirable to use a series of dilutions of test compounds. In some aspects, a kit is provided for performing this method. The kit comprises a first container comprising HIV Vpr or a fragment of Vpr known to interact with AIF; and a second container comprising AIF or a fragment of AIF which interacts with Vpr. Optionally, the kit may further comprise instructions for performing the test assay and/or a fourth container with a positive control such as anti-Vpr antibodies which competitively bind to Vpr with respect to AIF and/or anti-AIF antibodies which competitively bind to AIF with respect to Vpr.

Another aspect of the present invention relates to methods of identifying compounds that inhibit Vpr/AIF complexes from translocating to the nucleus of a cell. Cells known to produce or exposed to Vpr are contacted with test compounds. The level of Vpr and/or AIF in the nucleus and/or the level of Vpr and/or AIF in the cytoplasm is measured and compared to the corresponding level from cells not contacted with the test compound. In some embodiments of the invention, the preferred concentration of test compound is between 1 µM and 500 µM. A preferred concentration is 10 µM to 100 µM. In some preferred embodiments, it is desirable to use a series of dilutions of test compounds.

EXAMPLE

The following sequences identified by accession number and references are incorporated herein by reference.

| VPR | AJ404325 | vpr, gag, pol, vif, vpu, env, and nef |
|-----|----------|---------------------------------------|
| VPR | AF316862 | vif, vpr (Cameroon isolate) |
| VPR | AF325763 | vif, vpr (South African isolate) |
| AIF | XM 010246 | also called "programmed cell death 8" or "PDCD8" |
| AIF | NM 004208 | |

The invention claimed is:

1. A method of identifying compounds that inhibit HIV Viral Protein R (Vpr) binding to Apoptosis-inducing Factor (AIF) comprising a test assay that comprises the steps of:
   i) contacting a) isolated HIV Vpr and b) isolated AIF in the presence of c) a test compound and
   ii) comparing the level of isolated HIV Vpr binding to isolated AIF to the level of isolated HIV Vpr binding to isolated AIF in the absence of said test compound.

2. The method of claim 1 further comprising a positive control assay that comprises the steps of:
   i) contacting a) isolated HIV Vpr and b) isolated AIF in the presence of c) anti-Vpr antibodies which competitively bind to Vpr with respect to AIF and/or anti-AIF antibodies which competitively bind to AIF with respect to Vpr.

3. The method of claim 1 wherein the concentration of test compound is between 1 µM and 500 µM.

4. The method of claim 1 wherein the concentration of test compound is between 10 µM and 100 µM.

5. The method of claim 1 wherein a series of test assays are performed using a series of dilutions of test compounds.

* * * * *